US012594142B2

(12) United States Patent
Armand et al.

(10) Patent No.: US 12,594,142 B2
(45) Date of Patent: Apr. 7, 2026

(54) GUIDING SYSTEM FOR A SURGICAL ROBOTIC SYSTEM

(71) Applicant: ECENTIAL ROBOTICS, Gieres (FR)

(72) Inventors: David Armand, Saint Egreve (FR); François Girault, Grenoble (FR); Marc Bereau, Revel (FR)

(73) Assignee: ECENTIAL ROBOTICS, Gieres (FR)

( * ) Notice: Subject to any disclaimer, the term of this patent is extended or adjusted under 35 U.S.C. 154(b) by 366 days.

(21) Appl. No.: 18/559,896

(22) PCT Filed: May 20, 2022

(86) PCT No.: PCT/EP2022/063678
§ 371 (c)(1),
(2) Date: Nov. 9, 2023

(87) PCT Pub. No.: WO2022/243495
PCT Pub. Date: Nov. 24, 2022

(65) Prior Publication Data
US 2024/0382284 A1 Nov. 21, 2024

(30) Foreign Application Priority Data

May 21, 2021 (EP) ..................................... 21305672

(51) Int. Cl.
*A61B 90/50* (2016.01)
*A61B 34/30* (2016.01)
(52) U.S. Cl.
CPC .............. *A61B 90/50* (2016.02); *A61B 34/30* (2016.02)
(58) Field of Classification Search
CPC .......... A61B 17/17; A61B 2017/00477; A61B 2034/305; A61B 34/30; A61B 90/50
See application file for complete search history.

(56) References Cited

U.S. PATENT DOCUMENTS

2007/0055291 A1* 3/2007 Birkmeyer ......... A61B 17/1671
606/130
2012/0022535 A1 1/2012 Mayer
(Continued)

FOREIGN PATENT DOCUMENTS

EP 3821843 A1 5/2021

OTHER PUBLICATIONS

European Search Report in related EP Application No. 21305672, mailed Nov. 4, 2021.

(Continued)

*Primary Examiner* — Scott Luan
(74) *Attorney, Agent, or Firm* — Thomas | Horstemeyer, LLP

(57) ABSTRACT

The invention relates to a guiding system for a surgical robotic system, comprising a tool guide (11), a tool (30), an intermediate part (60) mounted on the tool (30), and first and second coupling links (21, 22), and presenting: —a first guiding configuration in which the first coupling link (21, 22) couples the intermediate part (60) and the tool guide (11) so that both are mobile relative to each other according to a unique first degree of freedom corresponding to a translation along a tool guide axis (X); and —a second guiding configuration in which the second coupling link (22) couples the intermediate part (60) and the tool guide (11) so that both are mobile relative to each other according to the first degree of freedom and according to at least one additional degree of freedom.

22 Claims, 9 Drawing Sheets

(56)  References Cited

U.S. PATENT DOCUMENTS

| | | | |
|---|---|---|---|
| 2016/0120611 | A1 | 5/2016 | Lohmeier |
| 2018/0353248 | A1 | 12/2018 | Bowling |

OTHER PUBLICATIONS

PCT Search Report in related PCT Application No. PCT/EP2022/063678, mailed Sep. 2, 2022.

* cited by examiner

GUIDING SYSTEM FOR A SURGICAL ROBOTIC SYSTEM

CROSS REFERENCE TO RELATED APPLICATIONS

This application is the 35 U.S.C. § 371 national stage application of PCT Application No. PCT/EP2022/063678, filed May 20, 2022, which application claims the benefit of European Application No. EP 21305672.4 filed May 21, 2021, both of which are hereby incorporated by reference herein in their entireties.

The present invention relates to a guiding system for a surgical robotic system, allowing the guiding of a tool by the surgical robotic system.

GENERAL TECHNICAL FIELD AND PRIOR ART

Surgical robotic systems are frequently used during surgical interventions, in order to assist a surgeon. The surgical robotic system may guide the positioning and orienting of a surgical tool for the surgeon.

The surgical robotic system comprises a surgical robotic arm, comprising an end effector holding a tool guide. The tool guide is to be placed with a given position and orientation relative to a surgical target. The surgeon can couple a surgical tool to the tool guide so that once the tool guide is placed relative to the surgical target, the surgical robotic system assists the surgeon in the guiding of the tool. Thus, the surgeon may maneuver the surgical tool with the right position and orientation relative to the surgical target during the surgery.

The surgeon may use the surgical robotic system in order to drill one or several holes into one or several bones of a patient, and then to implant a screw into each respective drilled hole. The surgical target corresponds to a specific position and orientation of the hole to be drilled on a bone such as a vertebra, or a fractured bone of the patient. For example, in spine surgery, several surgical targets may be located on several vertebrae of the patient.

The tool guide maintains the tool in a specific position and orientation relative to the surgical target in order to precisely guide the surgeon into drilling the hole and then implanting the screw. Thus, the surgical robotic system assists the surgeon in drilling the hole and then implanting the screw into the drilled hole.

However, a problem may occur during the guiding of the tool by the tool guide of the surgical robotic system. For example, a misalignment can exist or appear between the tool and the surgical target, such that the surgical target and the tool are not coaxial, and/or are not correctly positioned relative to each other. Such a misalignment may occur because of mechanical inaccuracies, movements of the bone during drilling or screwing or between drilling and screwing, etc. Such a misalignment can negatively impact the surgical procedure and possibly the final result of the surgical procedure.

For example, when the surgical robotic system assists the surgeon in implanting a screw into a drilled hole, the screw may not be perfectly coaxial with the drilled hole due to such misalignments. The misalignment between the screw and the surgical target may cause an undesirable locking to occur between the screwdriver and the screw engaged in the drilled hole, in a manner which makes it difficult to decouple the screw and screwdriver from each other. Another problem caused by such misalignment may be the difficulty for the surgeon to easily find the hole with the screw.

GENERAL PRESENTATION OF THE INVENTION

A general aim of the invention is to propose a guiding system allowing an improved guiding of a surgical robotic system.

According to a first aspect, the invention is directed towards a guiding system for a surgical robotic system, comprising a tool guide extending substantially around a tool guide axis, a tool extending substantially around a tool axis, an intermediate part mounted on the tool so that the tool and the intermediate part are integral in translation and so that the tool is mobile relative to the intermediate part in rotation around the tool axis, and first and second coupling links adapted to couple the intermediate part and the tool guide, wherein the guiding system presents:

a first guiding configuration in which the first coupling link couples the intermediate part and the tool guide so that the intermediate part and the tool guide are mobile relative to each other according to a unique first degree of freedom, the first degree of freedom corresponding to a translation along the tool guide axis; and a second guiding configuration in which the second coupling link couples the intermediate part and the tool guide so that the intermediate part and the tool guide are mobile relative to each other according to the first degree of freedom and according to at least one additional degree of freedom.

Some preferred but not limitative features of the guiding system described above are the following, taken individually or in combination:

the at least one additional degree of freedom comprises an inclination of the tool relative to the tool guide axis;

the at least one additional degree of freedom comprises a translation of the tool in a plane perpendicular to the tool guide axis;

the second coupling link is at least partially made of an elastic material, such that a deformation of said elastic material of the second coupling link allows said translation of the tool in the plane perpendicular to the tool guide axis;

the first coupling link and/or the second coupling link includes a slide link, wherein the slide link is directed along the tool guide axis;

the first coupling link and/or the second coupling link includes a ball joint;

the first coupling link includes the second coupling link and an additional coupling link;

the tool is a screwdriver having a handle and a shaft extending from the handle;

the first and/or second coupling links and the intermediate part are rigidly secured to each other so as to be moved together;

the first and second coupling links are configured so that a transition between the first guiding configuration and the second guiding configuration is achieved by translating the first and second coupling links relative to the tool guide along the tool guide axis;

the first coupling link is adapted to be located inside the tool guide in the first guiding configuration and at least partially outside the tool guide in the second guiding configuration;

the tool and the intermediate part are adapted to be at least partially inserted substantially radially inside the tool guide, the first and second coupling links being arranged on the intermediate part;

the tool is adapted to be mounted radially outside the tool guide, the first and second coupling links being at least partially inserted in sliding engagement within the tool guide and comprising a connecting section extending radially outwardly to mechanically connect the first and second coupling links to the intermediate part;

the guiding system further comprises blocking means adapted to prevent a rotation of the intermediate part relative to the tool guide around the tool axis;

the tool guide comprises a tracker adapted to be detected by a tracking system in order to determine a position and orientation of the tool guide relative to a surgical target;

the tool comprises a tracker adapted to be detected by a tracking system in order to determine a position and orientation of the tool relative to the tool guide and/or to the surgical target.

According to a second aspect, the invention is directed towards a surgical robotic system, comprising a robotic arm comprising the guiding system according to the first aspect, a tracking system configured to determine a position and orientation of the tool guide and/or the tool relative to a surgical target, a control unit coupled to the tracking system and configured to control the robotic arm to align the tool with the surgical target, and a display unit adapted to configure a guiding of the tool guide and/or the tool.

According to a third aspect, the invention is directed towards a method for guiding a tool with a surgical robotic system according to the second aspect relative to a surgical target, wherein the surgical target comprises a surgical target channel directed along a surgical target axis, wherein the method comprises the following steps:

S1: estimating a position of the tool relative to the surgical target, comprising a step S11 of detecting, by a tracking system, at least one tool guide tracker mounted in a fixed relationship relative to the tool guide and at least one patient tracker mounted in a fixed relationship relative to the surgical target;

S2: positioning the tool guide so that the tool is positioned at a predetermined distance from the surgical target channel;

S22: orienting the tool guide so that the tool axis is substantially aligned with the surgical target axis;

S3: guiding the tool in the first guiding configuration so as to partially insert said tool inside the surgical target channel;

S4: guiding the tool in the second guiding configuration so as to insert said tool deeper inside the surgical target channel.

Some preferred but not limitative features of the method described above are the following, taken individually or in combination:

the step S4 of guiding the surgical robotic system in the second guiding configuration comprises a step S41 of adjusting a relative position and/or orientation of the tool with respect to the surgical target in the at least one additional degree of freedom, wherein said step S41 is performed manually by a user of the surgical robotic system;

transitioning the surgical robotic system from the first guiding configuration to the second guiding configuration is performed by translating along the tool guide axis the first and second coupling links relative to the tool guide along a predetermined transition length;

the predetermined distance from the surgical target channel at which the tool is positioned in step S2 is determined depending at least on a length of the tool and a length of guiding in first guiding configuration, wherein the length of guiding in first guiding configuration corresponds substantially to the predetermined transition length;

the tool is a screwdriver having a handle and a shaft extending from the handle, wherein the guiding system further comprises a screw adapted to be removably attached to a tip of the shaft, wherein the predetermined distance from the surgical target channel at which the tool is positioned in step S2 is further determined depending on a length of the screw.

PRESENTATION OF THE FIGURES

Other features and advantages of the invention will emerge from the following description, which is purely illustrative and non-limiting and must be considered with respect to the appended figures in which.

DESCRIPTION OF SEVERAL EMBODIMENTS

Figure 1:
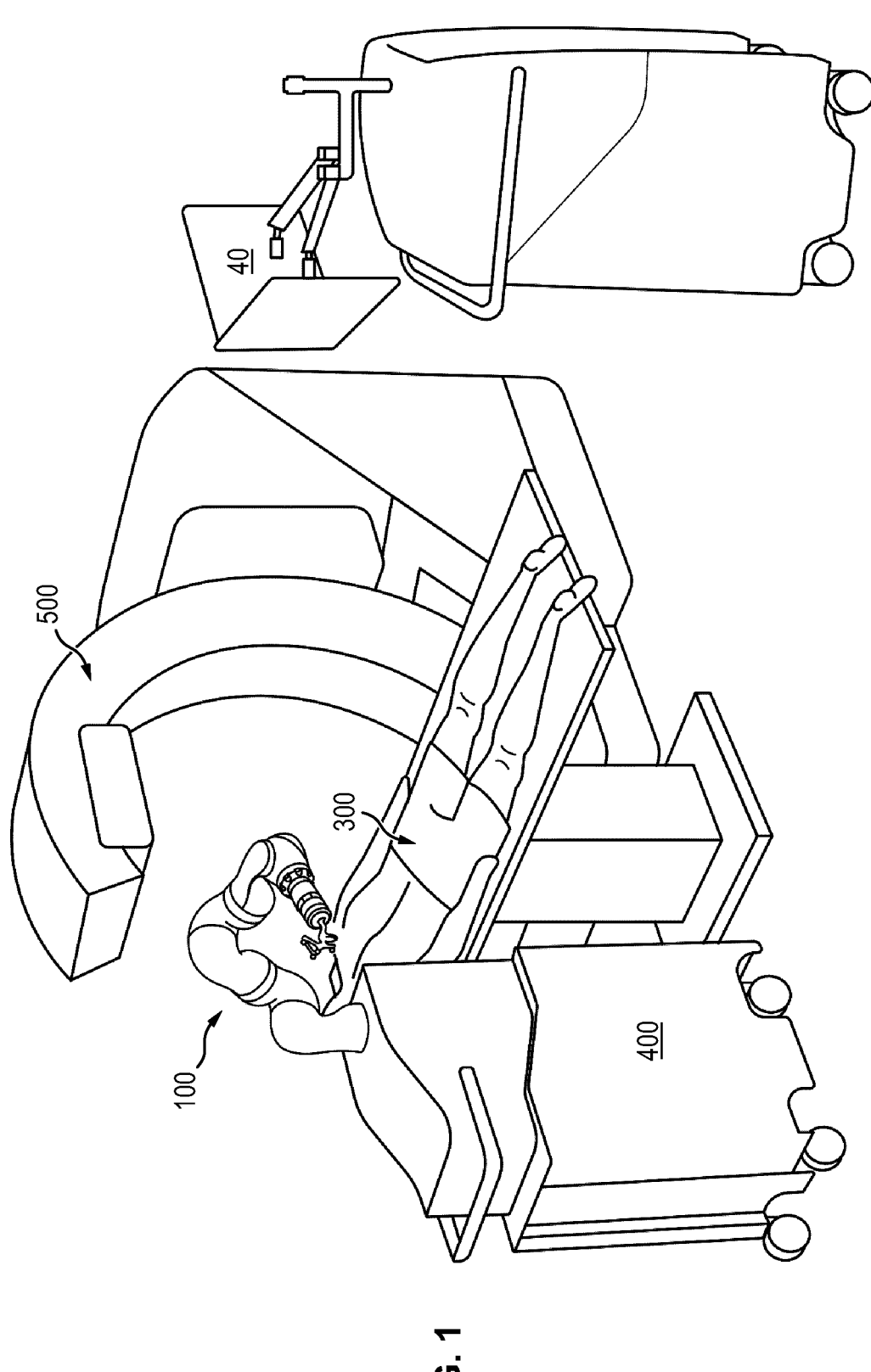
FIG. 1 is a perspective view of a surgical robotic system according to an embodiment of the invention.

A guiding system for a surgical robotic system is illustrated by way of a non-limiting example in FIGS. 2 to 10. The guiding system comprises a tool guide 11 extending substantially around a tool guide axis X, a tool 30 extending substantially around a tool axis T, an intermediate part 60 mounted on the tool 30 so that the tool 30 and the intermediate part 60 are integral in translation and so that the tool 30 is mobile relative to the intermediate part 60 in rotation around the tool axis T, and first and second coupling links 21, 22 adapted to couple the tool 30 and the tool guide 11.

The guiding system presents:

a first guiding configuration in which the first coupling link 21, 22 couples the intermediate part 60 and the tool guide 11 so that the intermediate part 60 and the tool guide 11 are mobile relative to each other according to a unique first degree of freedom, the first degree of freedom corresponding to a translation along the tool guide axis X; and a second guiding configuration in which the second coupling link 22 couples the intermediate part 60 and the tool guide 11 so that the intermediate part 60 and the tool guide 11 are mobile relative to each other according to the first degree of freedom and according to at least one additional degree of freedom.

The guiding system may be used during surgical interventions, in order to assist a surgeon in guiding the positioning and orienting of the intermediate part 60 coupled to the tool guide 11, thus of the tool 30, relative to a surgical target 50.

The surgical target 50, as illustrated by way of a non-limiting example in FIGS. 2, 3, 5 and 6, may be defined by a surgical target 50 position and/or a surgical target axis S. More specifically, the surgical target 50 may be a surgical target channel 51 oriented along the surgical target axis S and having a first end and a second end located opposite the first end, the surgical target 50 position corresponding to the position of the first end of the surgical target 50. The first end of the surgical target channel 51 may correspond to an entry point of the tool 30 into a bone 310 of a patient 300.

The terms proximal and distal are used in relation to a position along the surgical target axis S, so that during the surgical procedure, the distal end of an element is located closer to the surgical target 50, considering a distance along the surgical target axis S, than the proximal end of the same element.

The tool guide 11 extends substantially around the tool guide axis X. The tool guide 11 may be a tool guide channel, the tool guide 11 forming a substantially cylindrical sleeve around the tool guide axis X. The tool guide 11 is adapted to receive the first coupling link 21, 22 and/or the second coupling link 22. The tool guide 11 may also be adapted to receive the tool 30 and/or the intermediate part 60. The tool guide 11, more particularly the tool guide channel 11, may comprise a distal end and a proximal end located opposite the distal end.

The intermediate part 60 may extend around at least part of the tool 30, more particularly around at least part of a tool shaft 32 of the tool 30. The intermediate part 60 may extend substantially along the tool axis T. The intermediate part 60 may present a substantially hollow cylindrical shape configured to be arranged around the tool 30, more particularly around the tool shaft 32 of the tool 30, the tool shaft 32 passing through the intermediate part 60.

The tool 30 and the intermediate part 60 are mobile relative to each other only in rotation around the tool axis T, and are rigidly secured to each other in all the other degrees of freedom. In other words, the tool 30 can be rotated around the tool axis T inside the intermediate part 60, whatever the guiding configuration of the guiding system. Thus, for example when the tool 30 is a screwdriver, the screwdriver can be rotated around the screwdriver axis at any step of the surgical operation. However, the intermediate part 60 and the tool 30 are moved together in any translation, more particularly in translation along the tool guide axis X or in a plane perpendicular to the tool guide axis X, and in inclination relative to the tool guide axis X. Translating the tool 30 results in an identical translation of the intermediate part 60, and inclining the tool 30 relative to the tool guide axis X results in an identical inclination of the intermediate part 60.

In the first guiding configuration, the tool 30, the intermediate part 60 and the tool guide 11 may be substantially parallel to each other, located at a distance from each other, the tool guide axis X and the tool axis T being substantially parallel. Alternatively, the tool 30, the intermediate part 60 and the tool guide 11 may be substantially coaxial, the tool guide axis X and the tool axis T coinciding substantially. When the tool 30, the intermediate part 60 and the tool guide 11 are parallel, the tool guide 11 may be positioned by the surgical robotic system taking into account the distance between the tool guide 11 and the tool 30, in order to align the tool axis T with the surgical target axis S.

The surgeon may for example use the surgical robotic system in order to drill one or several holes into one or several bones 310 of the patient 300, and then to implant a screw 33 into each respective drilled hole.

First, the guiding system assists the surgeon in drilling the hole. The tool 30 is a drill. The surgeon can insert the drill into the tool guide 11 of the guiding system, or mount the drill outside the tool guide 11. The tool guide 11 allows positioning and orienting of the drill relative to the hole to be drilled, and guiding of the drill at the desired position and orientation during the drilling of the hole in the bone 310. Therefore, the guiding system assists the surgeon in drilling a hole intended to receive the screw 33 at the desired hole position, which corresponds to the position of the surgical target 50, and along the desired hole orientation, which corresponds to the orientation of the surgical target axis S.

Second, after the drilling is carried out, the guiding system assists the surgeon in implanting a screw 33 into the drilled hole. The tool 30 is a screwdriver. The screwdriver has a handle 31, and a shaft 32 extending from the handle 31. A screw 33 may be removably mounted to the tip of the shaft 32 of the screwdriver. The surgeon can insert the screwdriver into the tool guide 11 of the guiding system, or mount the screwdriver outside the tool guide 11. The tool guide 11 allows positioning of the screwdriver and screw 33 relative to the hole drilled in the bone 310, so that the surgeon can insert and screw the screw 33 into the hole. Therefore, the guiding system assists the surgeon in implanting the screw 33 in the drilled hole. The position and orientation of the surgical target 50 corresponds to the position and orientation of the hole drilled in the bone 310.

The first and second coupling links 21, 22 adapted to couple the intermediate part 60 and the tool guide 11 are mechanical linkages allowing certain movements of the intermediate part 60, thus of the tool 30, relative to the tool guide 11 and preventing other movements of the intermediate part 60, thus of the tool 30, relative to the tool guide 11.

The first guiding configuration and second guiding configuration allow to the guiding system to minimize the workload of the surgeon while efficiently assisting the surgeon, in order to optimize the guiding and the final result of the surgical procedure.

In the first guiding configuration, the intermediate part 60 and the tool guide 11 are mobile relative to each other according to a first degree of freedom corresponding to a translation along the tool guide axis X. Thus, in the first guiding configuration, the intermediate part 60, thus the tool 30, may be translated along the tool guide axis X while the tool guide 11 remains at a fixed position along the tool guide axis X, or vice versa the tool guide 11 may be translated along the tool guide axis X while the intermediate part 60, thus the tool 30, remains at a fixed position along the tool guide axis X. Additionally or alternatively, the intermediate part 60, thus the tool 30, and the tool guide 11, may each simultaneously be translated along the tool guide axis X, in opposite directions or in a same direction but along different distances, so that the relative position of the intermediate part 60 and the tool guide 11 along the tool guide axis X varies.

In the first guiding configuration, the first degree of freedom is a unique first degree of freedom. Thus, the intermediate part 60 and the tool guide 11 cannot be moved relative to each other in any other direction or orientation than in translation along the tool guide axis X. The tool 30 can therefore only be moved relative to the tool guide according to two degrees of freedom, that is to say in translation along the tool guide axis X, which corresponds to the first degree of freedom, and also in rotation around the tool axis T. For example, an orientation of the intermediate part 60, thus of the tool 30 relative to the tool guide 11, cannot be modified, and a position of the intermediate part 60, thus of the tool 30, relative to the tool guide 11 in a direction other than the direction of the tool guide axis X cannot be modified. The first guiding configuration thus offers a rigid guiding of the intermediate part 60, thus of the tool 30.

During a surgical intervention, the tool 30 may be placed in a predetermined position and orientation relative to the surgical target 50 according to the operation to perform. Then, the guiding system in the first guiding configuration rigidly guides the intermediate part 60, thus the tool 30. For example, the guiding system rigidly guides the drill into the bone 310 so as to drill a hole in the bone 310, or rigidly guides the screwdriver so as to implant the screw 33 into the drilled hole. In the first guiding configuration, the intermediate part 60 and the tool guide 11 are mobile relative to each other only in translation along the tool guide axis X, that is to say according to the unique first degree of freedom. The tool 30, for example the drill or the screwdriver, is also mobile in rotation around the tool axis T relative to the tool guide 11.

Thus, in the first guiding configuration, the workload of the surgeon is minimized, as the position and inclination of the tool 30 relative to the tool guide 11 is managed by the guiding system, the surgeon having leeway to influence only one degree of freedom.

In the second guiding configuration, the intermediate part 60, thus the tool 30 and the tool guide 11 are also mobile relative to each other according to at least one additional degree of freedom. Thus, the intermediate part 60, thus the tool 30, and the tool guide 11, may be moved relative to each other in translation along the tool guide axis X, and may also be moved relative to each other according to at least one other degree of freedom, for example in orientation or in translation along a direction other than the direction of the tool guide axis X.

Thus, the second guiding configuration offers a more flexible guiding of the intermediate part 60, thus of the tool 30. The guiding system thus allows the surgeon to maintain some leeway in the guiding of the tool 30, in position and/or orientation, relative to the tool guide 11, more specifically in at least one position and/or orientation other than the translation along the tool guide axis X and rotation around the tool axis T.

A more flexible guiding allows to prevent problems during the guiding of the tool 30 by the guiding system. Especially, it may be necessary for the surgeon to adjust a position and orientation of the tool 30 relative to the tool guide 11 in order to align the tool 30 in position and/or orientation relative to the surgical target 50. For example, if a misalignment may exist or appear between the tool 30 and the surgical target 50, such that the surgical target 50 and the tool 30 are not coaxial and/or are not correctly positioned relative to each other. Such a misalignment may occur because of mechanical inaccuracies, movements of the bone 310 during drilling or screwing or between drilling and screwing, etc.

A relatively flexible guiding, as allowed by the second guiding configuration, allows the surgeon to rectify such a misalignment, that is to say to adjust a position and/or orientation of the tool 30 relative to the tool guide 11 in order to align the tool 30 in position and/or orientation relative to the surgical target 50.

For example, when the surgical robotic system assists the surgeon in implanting a screw 33 in a drilled hole, the drilled hole and the screw 33 may not be perfectly coaxial due to misalignments. This may cause an undesirable locking to occur between the screwdriver and the screw 33 engaged in the drilled hole, in a manner which makes it difficult to decouple the screw 33 and the screwdriver from each other.

The second guiding configuration may be used for example after the screwdriver has been translated along a certain distance, especially once the screw 33 is at least partially inserted into the hole, the guiding system being in the first guiding configuration in order to partially insert the screw 33 into the hole. Once the guiding system is in the second guiding configuration, the surgeon may thus manipulate the screwdriver with ease according to the at least one additional degree of freedom when the screwdriver moves inwards so as to continue to implant the screw 33 in the drilled hole. Thus, the surgeon may correct a potential misalignment between the screw 33 and the drilled hole, therefore preventing the undesirable locking between screwdriver and the screw 33 engaged in the drilled hole.

If the guiding system is in the first guiding configuration and the surgeon notices a misalignment or a risk of undesirable locking between the screw 33 and the screwdriver, the surgeon may move the guiding system to the second guiding configuration. Then, the surgeon may adjust a position and/or orientation of the tool 30 relative to the tool guide 11 so as to align to the tool 30 with the surgical target 50. Alternatively, the guiding system may automatically be transitioned from the first guiding configuration to the second guiding configuration after the tool 30 has been moved along a certain distance towards the surgical target 50 along the tool guide axis X.

The at least one additional degree of freedom may comprise an inclination of the intermediate part 60, thus of the tool 30, relative to the tool guide axis X.

Figure 4:
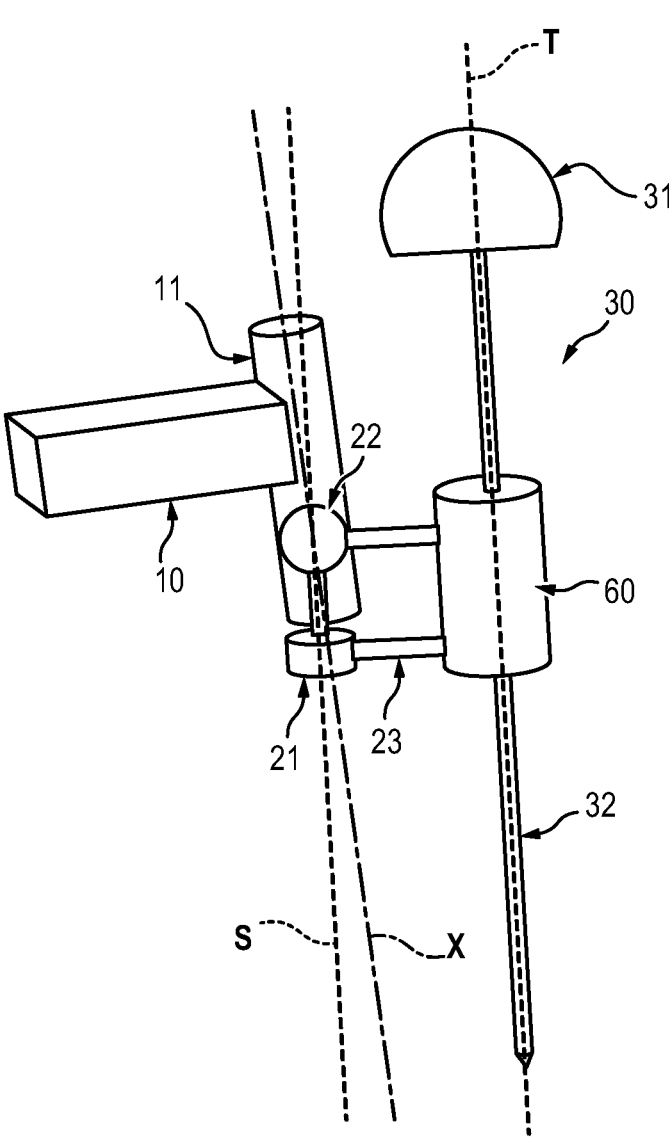
FIG. 4 is a perspective view of a guiding system for a surgical robotic system according to an embodiment of the invention, the guiding system being in the second guiding configuration.
Figure 5:
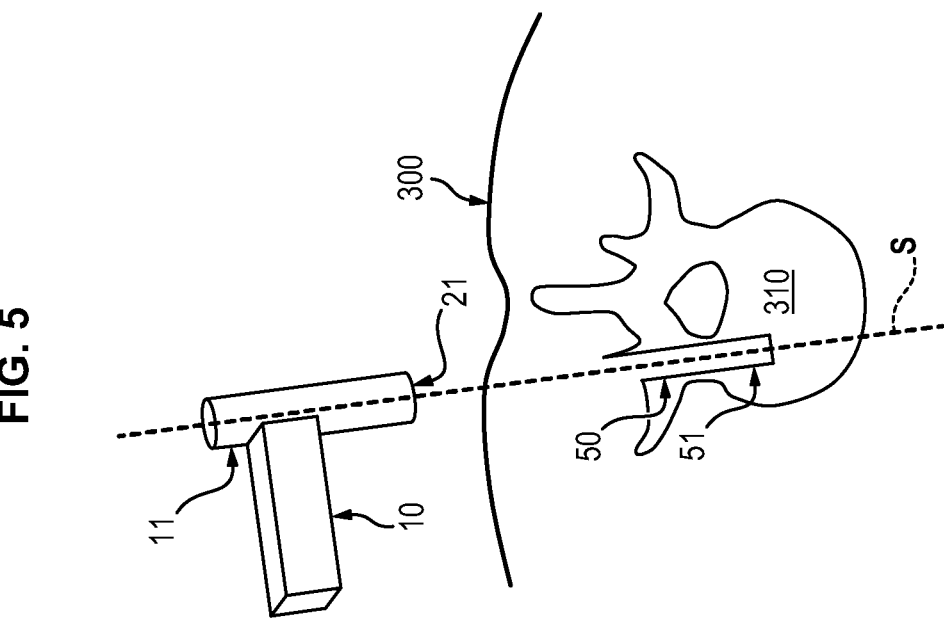
FIGS. 5 and 6 are perspective views of a surgical target and part of a guiding system for a surgical robotic system according to an embodiment of the invention.

Thus, the tool 30 and the tool guide 11 in the second configuration are mobile relative to each other in translation along the tool guide axis X, in rotation around the tool axis T, and in angular inclination relative to the tool guide axis X. The tool 30 may be inclined with respect to the tool guide axis X so as to form an inclination angle relative to the tool guide axis X, the tool 30 thus having an orientation which differs from the orientation of the tool guide 11. A non-limiting example of a tool 30 having a non-zero angular inclination, or orientation, relative to the tool guide 11, is illustrated in FIG. 4. The axis labelled S' in FIG. 4 corresponds to an axis which is parallel to the surgical target axis S.

Therefore, if the tool 30 is not coaxial with the surgical target 50 while the guiding system is in the second guiding configuration, that is to say when the tool axis T forms a non-zero inclination angle with respect to the surgical target axis S, the orientation of the tool 30 may be modified so as to align the tool axis T with the surgical target axis S. For example, the orientation of the drill may be adjusted if the drill is not coaxial with the hole to be drilled. Similarly, the orientation of the screwdriver may be adjusted if the screwdriver is not coaxial with the drilled hole into which the screw 33 is to be inserted.

In addition, or alternatively, the at least one additional degree of freedom may comprise a translation of the intermediate part 60, thus of the tool 30, in the plane perpendicular to the tool guide axis X, for example a translation of the intermediate part 60, thus of the tool 30 along at least one direction of the plane perpendicular to the tool guide axis X.

Thus, if the tool 30 does not face the surgical target 50, for example if the tool 30 is spaced apart with respect to the surgical target 50 in a direction perpendicular to the tool guide axis X, then a position of the tool 30 may be adjusted so that the tool 30 faces the surgical target 50, for example so that a tip of the tool 30 is only separated from the first end of the surgical target 50 by a predetermined distance along the tool guide axis X. For example, the position of the tool 30 may be adjusted so that the tool 30 is substantially coaxial with the surgical target 50, the tool axis T and the surgical target axis S being substantially coaxial.

Such a second coupling link 22 allows to compensate a misalignment in position and/or orientation, between the tool 30 and the surgical target 50.

The first coupling link 21, 22 and/or the second coupling link 22 may include a slide link, wherein the slide link is directed along the tool axis T, the tool axis T corresponding to the tool guide axis X in the first guiding configuration. The slide link may allow a cylindrical contact with the tool guide 11, so as to allow a translation along the tool guide axis X. The first coupling link 21, 22 and/or the second coupling link 22 is thus slidable inside the tool guide channel 11.

The first coupling link 21, 22 and/or the second coupling link 22 may include a ball joint. The ball joint may allow a spherical connection with the tool guide 11, so as to allow a rotation around the tool guide axis X, and preferably further rotation around one or more supplementary axes of rotation so as to allow inclination of the tool 30 relative to the tool guide axis X.

The first coupling link 21, 22 and/or the second coupling link 22 may be rigidly secured to each other so as to be moved together.

The first coupling link 21, 22 may comprise at least one slide link. For example, the first coupling link 21, 22 may comprise two slide links substantially arranged along the tool guide axis X, as illustrated by way of a non-limiting example in FIG. 7c. At least one slide link of the first coupling link 21, 22 has an outer diameter which corresponds substantially to an inner diameter of the tool guide channel 11. Therefore, the first coupling link 21, 22 can only be moved inside the tool guide channel 11 according to the first degree of freedom, that is to say in translation along the tool guide axis X. Thus, the two slide links of the first coupling link 21, 22 ensure the first guiding configuration of the guiding system.

The first coupling link 21, 22 may comprise at least one ball joint. For example, the first coupling link 21, 22 may comprise two ball joints substantially arranged along the tool guide axis X, as illustrated by way of a non-limiting example in FIGS. 7b, 8a and 12a. At least one of the ball joints of the first coupling link 21, 22 has an outer diameter which corresponds substantially to an inner diameter of the tool guide channel 11. Therefore, the ball joints of the first coupling link 21, 22 can only be moved inside the tool guide channel 11 according to the first degree of freedom, that is to say in translation along the tool guide axis X. Thus, the two ball joints of the first coupling link 21, 22 ensure the first guiding configuration of the guiding system.

The first coupling link 21, 22 may comprise a ball joint and a slide link, as illustrated by way of a non-limiting example in FIGS. 7a, 8b, 12b and 12c. At least one of the ball joint or the slide link has an outer diameter which corresponds substantially to an inner diameter of the tool guide channel 11, so as to allow movement of the first coupling link 21, 22 inside the tool guide channel 11 only in translation along the tool guide axis X, thus ensuring the first guiding configuration of the guiding system.

The second coupling link 22 may have an outer dimension which is smaller than an inner dimension of the tool guide 11, so as to form a gap between the second coupling link 22 and the tool guide 11 when the second coupling link 22 is inserted into the tool guide 11. Thus, in the second guiding configuration, that is to say when the second coupling link 22 couples the intermediate part 60 and the tool guide 11, the intermediate part 60, thus the tool 30, may be translated along the tool guide axis X, and may also be translated in the plane perpendicular to the tool guide axis X along a distance corresponding to the gap formed between the second coupling link 22 and the tool guide 11. Thus, a small misalignment in position between the surgical target 50 and the tool 30 may be rectified.

Figure 11:
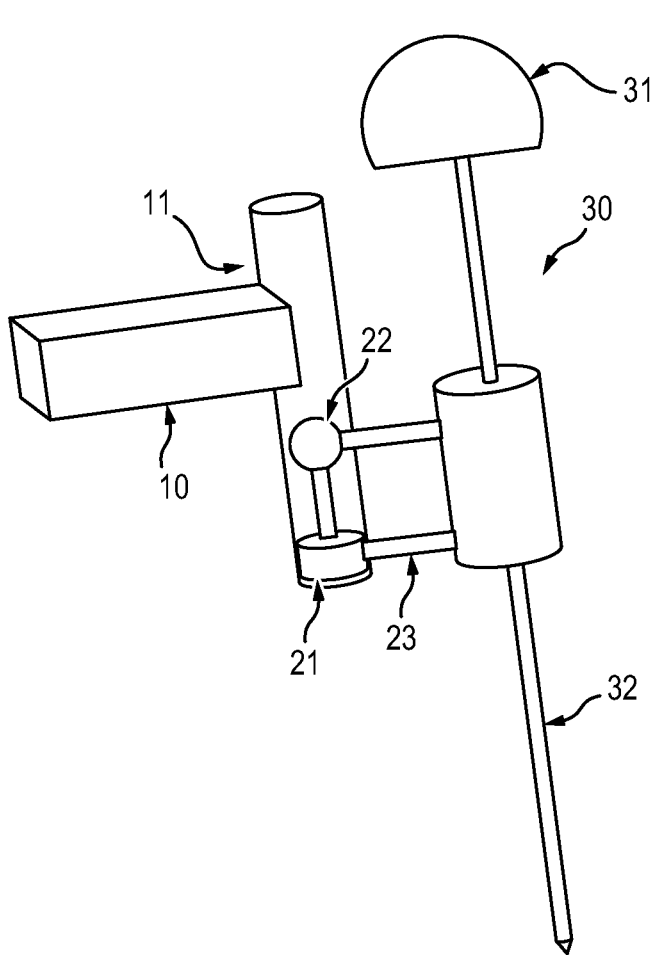
FIG. 11 is a perspective view of a guiding system for a surgical robotic system according to another embodiment of the invention, the guiding system being in the first guiding configuration.

More particularly, the second coupling link 22 may comprise a ball joint having a diameter smaller than a diameter of the tool guide channel 11, as illustrated by way of a non-limiting example in FIG. 11. Such a second coupling link 22 authorizes an inclination of the tool 30 relative to the tool guide axis X and a translation of the tool 30 in a plane perpendicular to the tool guide 11, in addition to the translation of the tool 30 and/or the tool guide 11 along the tool guide axis X, thus ensuring the second guiding configuration of the guiding system.

Alternatively, the second coupling link 22 is at least partially made of an elastic material, such that a deformation of said elastic material of the second coupling link 22 allows said translation of the intermediate part 60, thus of the tool 30 in the plane perpendicular to the tool guide axis. The elastic properties of the elastic material allow, via the elastic deformation of the elastic material, a translation of the second coupling link 22, thus of the tool 30, in the plane perpendicular to the tool guide axis X, along a distance corresponding to a maximum deformation of the second coupling link 22 in the corresponding direction. The second coupling link 22 may be entirely made of said elastic material. The elastic material may be silicon.

More specifically, the second coupling link 22 may be a slide link or a ball joint at least partially made of an elastic material. The slide link or the ball joint has an outer diameter which corresponds substantially to an inner diameter of the tool guide channel 11. The slide link or the ball joint may comprise a core made of a non-elastic material such as steel, and an outer envelope made of silicon, or may be entirely made of silicon.

Alternatively, or in addition, the second coupling link 22 may comprise a slide link having a diameter smaller than a diameter of the tool guide channel 11. Such a second coupling link 22 authorizes a translation of the intermediate part 60, thus of the tool 30, in a plane perpendicular to the tool guide 11, in addition to the translation of the tool 30 and/or the tool guide 11 along the tool guide axis X thus ensuring the second guiding configuration of the guiding system, but does not authorize an inclination of the intermediate part 60, thus of the tool 30, relative to the tool guide axis X.

Alternatively, a dimension of the second coupling link 22 may correspond substantially to a dimension of the tool guide channel 11. For example, the second coupling link 22 may be a ball joint having a diameter corresponding substantially to a diameter of the tool guide channel 11. Thus, the second coupling link 22 authorizes an inclination of the tool 30 relative to the tool guide axis X, in addition to the translation of the tool 30 and/or the tool guide 11 along the tool guide axis X, thus ensuring the second guiding configuration of the guiding system.

The first and second coupling links 21, 22 may be arranged around the intermediate part 60 and/or may be rigidly secured to the intermediate part 60. For example, when the first and second coupling links 21, 22 include a slide link, said slide link may present a substantially hollow cylindrical shape configured to be arranged around the intermediate part 60, the intermediate part 60 extending through said slide link.

In a first example of realization, the first coupling link 21, 22 may include the second coupling link 22 and an additional coupling link. Therefore, the number of coupling links of the guiding system is minimized and the guiding system is thus simplified. For example, the second coupling link 22 may be a slide link or a ball joint, and the first coupling link 21, 22 may include the slide link or ball joint of the second coupling link 22, and an additional coupling link such as an additional slide link 21 or an additional ball joint 21.

Figure 7C:
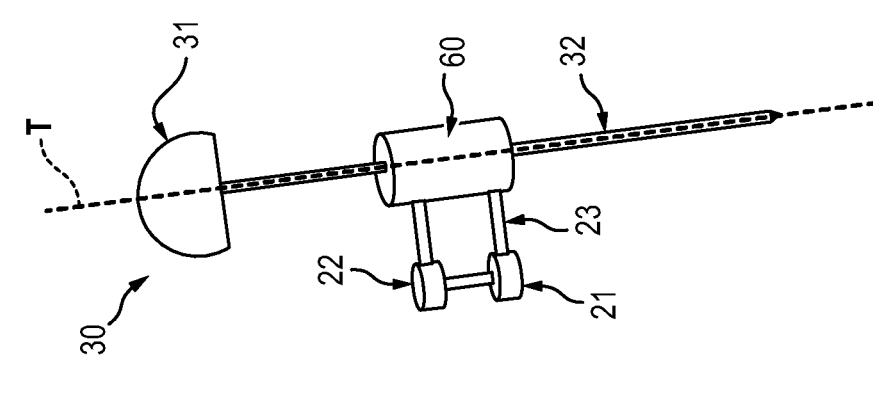
FIGS. 7a, 7b and 7c are perspective views of guiding systems for a surgical robotic system according to different embodiment of the invention, wherein the tool is adapted to be mounted radially outside the tool guide.
Figure 7B:
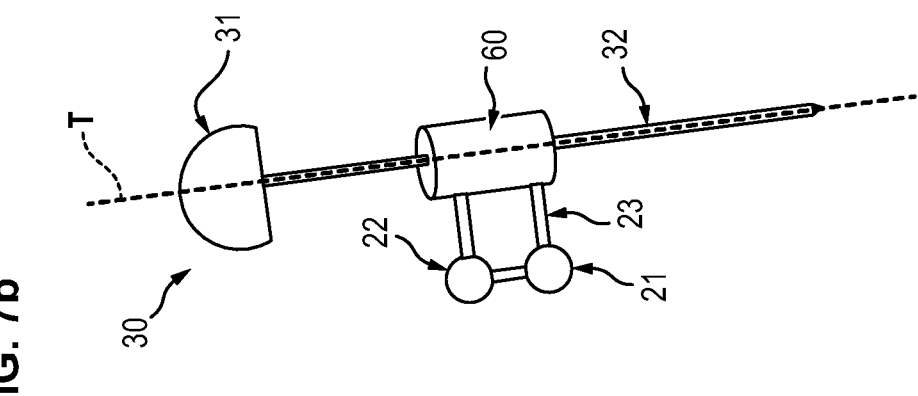
Figure 7A:
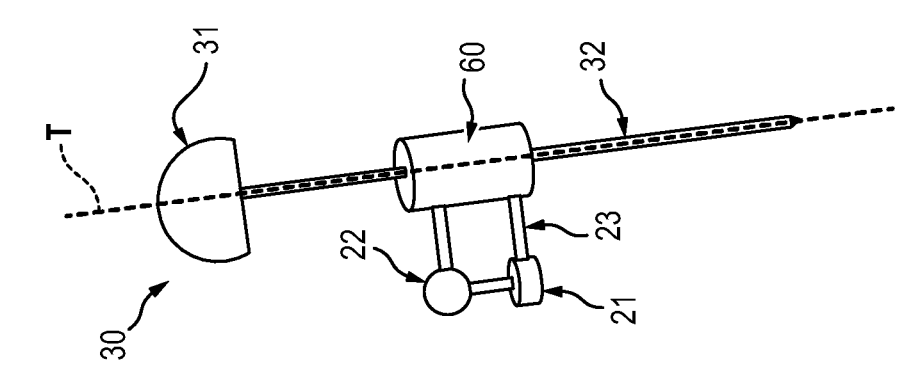
Figure 8B:
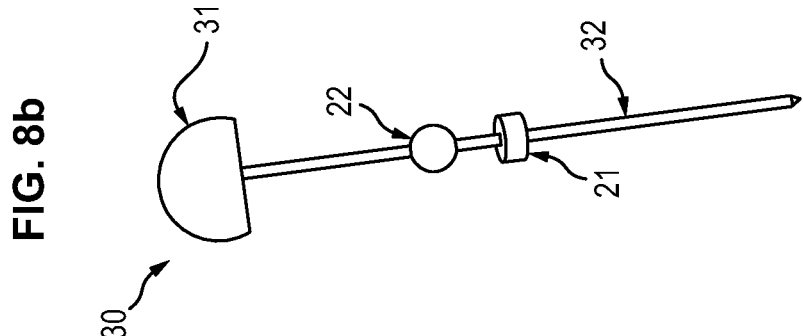
FIGS. 8a and 8b are perspective views of surgical robotic systems according to different embodiment of the invention.
Figure 8A:
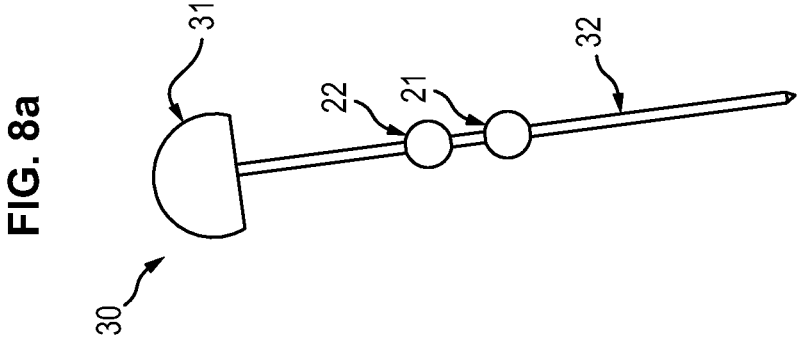
Figure 12C:
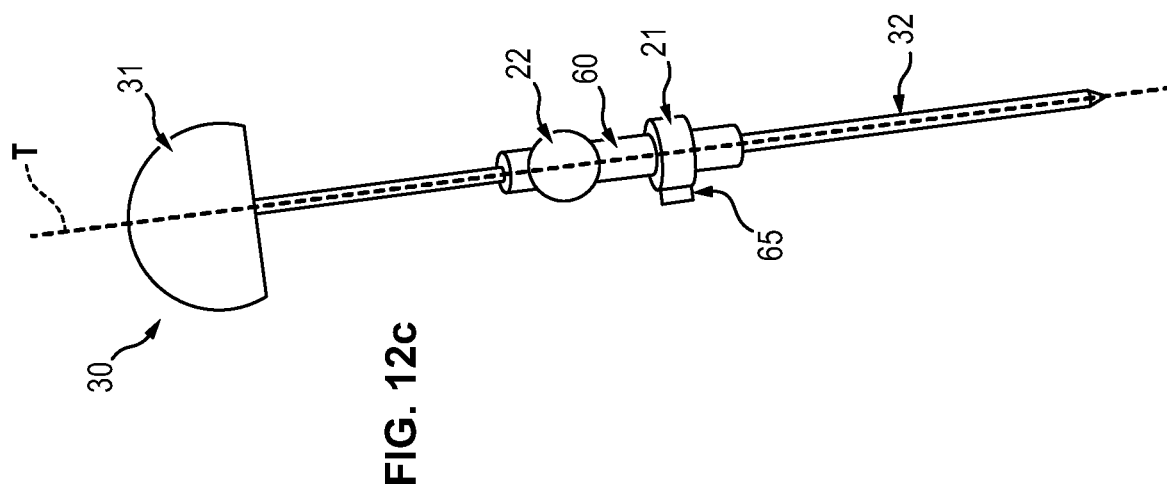
FIGS. 12a, 12b and 12c are perspective views of guiding systems for a surgical robotic system according to different embodiment of the invention, wherein the tool and the intermediate part are adapted to be at least partially inserted substantially radially inside the tool guide.
Figure 12B:
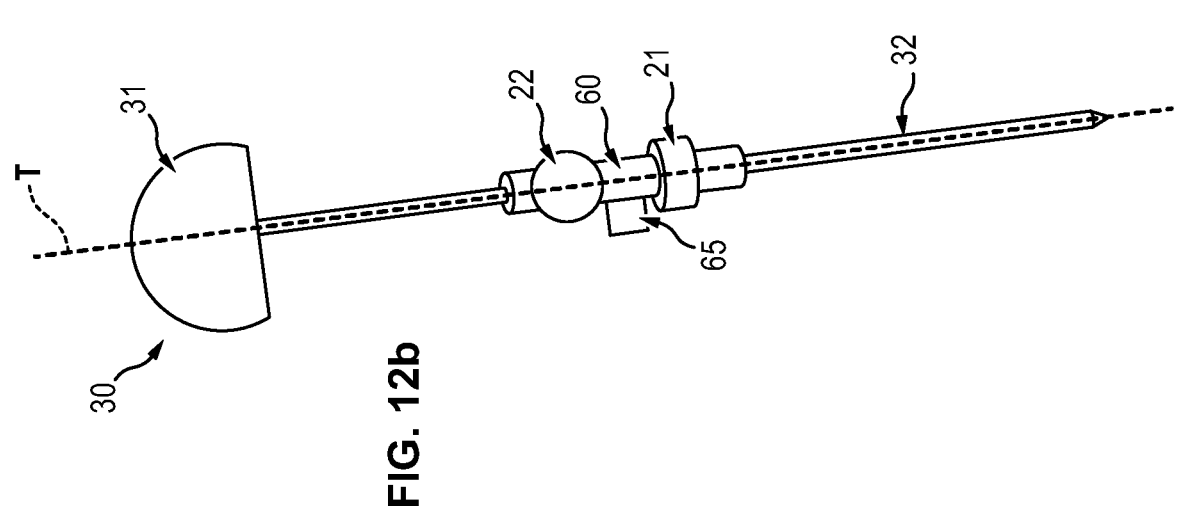
Figure 12A:
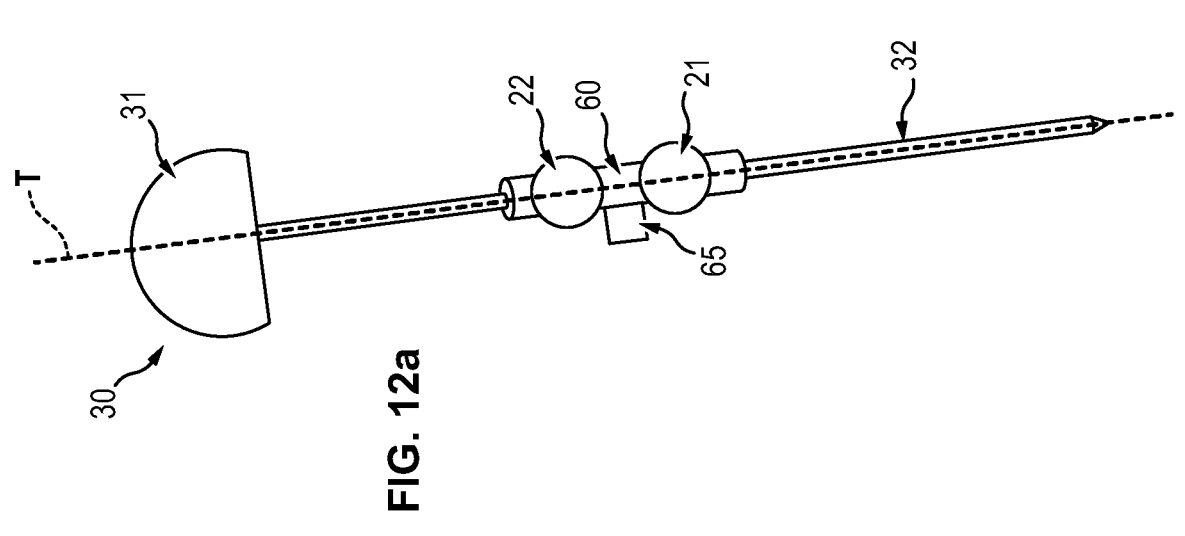

FIGS. 7b, 8a and 12a illustrate non-limiting examples in which the second coupling link 22 is a ball joint and the first coupling link 21, 22 comprises the ball joint of the second coupling link 22 and an additional coupling link in the form of an additional ball joint 21. FIGS. 7a, 8b, 12b and 12c illustrate non-limiting examples in which the second coupling link 22 is a ball joint and the first coupling link 21, 22 comprises the ball joint of the second coupling link 22 and an additional coupling link in the form of an additional slide link 21. FIG. 7c illustrates a non-limiting example in which the second coupling link 22 is a slide link and the first coupling link 21, 22 comprises the slide link of the second coupling link 22 and an additional coupling link in the form of an additional slide link 21.

The first coupling link 21, 22 may be adapted to be located inside the tool guide 11 in the first guiding configuration, both the second coupling link 22 and the additional coupling link 21 of the first coupling link 21, 22 being located inside the tool guide 11. The first coupling link 21, 22 may be adapted to be located at least partially outside the tool guide 11 in the second guiding configuration, only the second coupling link 22 being located inside the tool guide 11, the additional coupling link 21 of the first coupling link 21, 22 being located outside the tool guide 11. Thus, the first guiding configuration provides a rigid guiding while the second guiding configuration allows for a more flexible guiding.

In a second example of realization, the first coupling link 21, 22 and the second coupling link 22 are distinct coupling links. The first coupling link 21, 22 may be adapted to be located inside the tool guide 11 in the first guiding configuration, and to be located outside the tool guide 11 in the second guiding configuration.

In the first example of realization or in the second example of realization, the first and second coupling links 21, 22 may be configured so that a transition between the first guiding configuration and the second guiding configuration is achieved by translating the first and second coupling links 21, 22 relative to the tool guide 11 along the tool guide axis X.

Thus, the user may easily change a guiding configuration of the guiding system by a simple translation of the first and second coupling links 21, 22 along the tool guide axis X, therefore easily adapting the guiding configuration according to the guiding needs.

The translation may be of a few millimeters or a few centimeters along the tool guide axis X. For example, the surgeon can move the tool guide 11 a few centimeters away from the surgical target 50 so as to transition the guiding system from the first guiding configuration to the second guiding configuration. Once the guiding system is in the second guiding configuration, the surgeon may adjust a position and/or orientation of the tool 30 relative to the tool guide 11 so as to align to the tool 30 with the surgical target 50. Once the tool 30 is aligned with the surgical target 50, the surgeon may then move the tool guide 11 back a few centimeters along the tool guide axis X, in order to transition the guiding system from the second configuration to the first configuration.

More specifically, the first coupling link 21, 22 may be located closer to the distal end of the tool guide 11 than the second coupling link. When the first coupling link 21, 22 comprises the second coupling link 22 and an additional coupling link, the additional coupling link may be located closer to the distal end of the tool guide 11 than the second coupling link. Thus, when the tool 30, thus the intermediate part 60, is translated along the tool guide axis X towards the distal end of the tool guide 11 and/or when the tool guide 11 is translated in an opposite direction, the first coupling link 21, 22 or the additional coupling link of the first coupling link 21, 22 exits the tool guide channel 11 while the second coupling link 22 is still inside the tool guide channel 11, thus the system transitions from the first guiding configuration to the second guiding configuration.

The first and/or second coupling links 21, 22 and the intermediate part 60 may be rigidly secured to each other so as to be moved together.

Thus, a translation of the tool 30, thus of the intermediate part 60, along the tool guide axis X may correspondingly translate the first and/or second coupling links 21, 22 along the tool guide axis X, therefore achieving a transition between the first guiding configuration and the second guiding configuration. The transition between the first guiding configuration and the second guiding configuration is therefore even more easily achieved by the user.

The translation of the tool 30, thus of the intermediate part 60, and/or of the tool guide 11 relative to each other may be performed manually by the user of the guiding system, and/or automatically by the guiding system.

For example, a translation of the tool 30, thus of the intermediate part 60, along the tool guide axis X towards the surgical target 50 may cause the first coupling link 21, 22 or the additional coupling link of the first coupling link 21, 22 to exit the tool guide 11, thus transitioning the guiding system from the first guiding configuration to the second guiding configuration. A translation of the tool 30, thus of the intermediate part 60, along the tool guide axis X away from the surgical target 50 may cause the first coupling link 21, 22 or the additional coupling link of the first coupling link 21, 22 to enter the tool guide 11, thus transitioning the guiding system from the second guiding configuration to the first guiding configuration. Similarly, a translation of the tool guide 11 towards the surgical target 50 may cause the guiding system to transition from the second guiding configuration to the first guiding configuration, while a translation of the tool guide 11 relative to the tool 30, thus to the intermediate part 60, away from the surgical target 50 may cause the guiding system to transition from the first guiding configuration to the second guiding configuration. A simultaneous translation of the tool guide 11 and the tool 30, thus the intermediate part 60, in opposite directions along the tool guide axis X may cause the guiding system to transition between the first guiding configuration and the second guiding configuration.

In a first example embodiment illustrated in FIGS. 8*a*, 8*b*, 12*a*, 12*b* and 12*c*, the tool 30 and the intermediate part 60 are adapted to be at least partially inserted substantially radially inside the tool guide 11, the first and second coupling links 21, 22 being arranged on the intermediate part 60, for example around the intermediate part 60. The tool guide 11 is configured to receive the first and second coupling links 21, 22, the intermediate part 60 and the tool 30, the tool 30 being inserted inside the tool guide 11 by the user. The tool guide 11 maintains the tool 30 in the desired position and orientation during the surgery in order to allow guiding of the tool 30 by the surgical robotic system. In the first guiding configuration, the tool axis T and the tool guide axis X substantially coincide. The first and second coupling links 21, 22 may be rigidly secured to the intermediate part 60, so that the first and second coupling links 21, 22 are moved together with the intermediate part 60.

In a second example embodiment illustrated in FIGS. 2, 3, 4, and 7*a* to 7*c*, the tool 30 is adapted to be mounted radially outside the tool guide 11, the first and second coupling links 21, 22 being at least partially inserted in sliding engagement within the tool guide 11 and comprising a connecting section 23 extending radially outwardly to mechanically connect the first and second coupling links 21, 22 to the intermediate part 60. The tool 30 and the intermediate part 60 are thus located outside the tool guide 11, that is to say radially outwardly relative to the tool guide 11, and the first and second coupling links 21, 22 are located at least partially inside the tool guide 11. The tool guide 11 maintains the intermediate part 60, thus the tool 30, in the desired position and orientation during the surgery in order to allow guiding of the tool 30 by the surgical robotic system. In the first guiding configuration, the tool axis T and the tool guide axis X are substantially parallel, the tool axis T being spaced apart outwardly with respect to the tool guide axis X by the connecting section 23. The connecting section 23 may rigidly fix the intermediate part 60 to the first and second coupling links 21, 22, so that the first and second coupling links 21, 22 are moved together with the intermediate part 60.

The guiding system may further comprise blocking means 65 adapted to prevent a rotation of the intermediate part 60 relative to the tool guide 11 around the tool axis T. The blocking means 65 may comprise a pin or rib and a groove or slot, the pin or rib 65 being configured to cooperate with the groove or slot so as to block a rotation of the intermediate part 60 relative to the tool guide 11.

The groove or slot and the pin or rib 65 are configured so that when the intermediate part 60, the first and second coupling links 21, 22 and the tool 30 are located inside the tool guide 11, the pin or rib 65 cooperate with the groove or slot, the pin or rib 65 being able to translate in the groove or slot along the tool guide axis X while the groove or slot prevents a rotation of the pin or rib 65 around the tool guide axis X.

The pin or rib 65 may extend mainly along a main direction, a length of the pin or rib 65 corresponding to a dimension of the pin or rib 65 along the main dimension. The pin or rib 65 may be mounted on the intermediate part 60, on the first coupling link 21, 22, or on the second coupling link 22. The pin or rib 65 is configured so as to extend radially outwardly away from the element on which it is mounted, substantially in the main direction.

The groove or slot may be formed in the tool guide 11, more particularly in an inner face of the tool guide channel 11.

The groove or slot has a length corresponding to a dimension along the tool guide axis X of the groove or slot, which corresponds to a main dimension of the groove or slot. The length of the groove is less than the length of the tool guide channel 11, and the groove does not extend at the distal end of the tool guide 11, that is to say does not open at the distal end of the tool guide 11. The length of the slot is less than or equal to the length of the tool guide channel 11, and the slot extends at the distal end of the tool guide 11, that is to say opens at the distal end of the tool guide 11.

The groove or slot has a depth corresponding to a radial dimension of the groove or slot. The depth or the groove or slot may be substantially equal to the main dimension of the pin or rib 65, so that the groove or slot allows only a translation of the pin or rib 65 along the tool guide axis X. The depth or the groove or slot may be greater than the main dimension of the pin or rib 65, so that the groove or slot allows a translation of the pin or rib 65 along the tool guide axis X and also allows movement of the intermediate part 60 relative to the tool guide 11 according to the at least one additional degree of freedom, for example so as to allow an inclination of the intermediate part 60 compared to the tool guide axis X and/or a translation of the intermediate part 60 in the plane normal to the tool guide axis X. The groove or slot may have a width corresponding substantially to a width of the pin or rib 65, such that the groove or slot prevents the pin or rib 65 from being moved in rotation around the tool axis T relative to the tool guide 11. Directions of the width, of the length and of the depth of the groove or slot are perpendicular to one another.

For example, when the pin or rib 65 is mounted so that it remains in the groove or slot of the tool guide 11 when the guiding system is in the second guiding configuration, the depth of the groove or slot may be slightly greater than the dimension of the pin or rib 65 along the main direction, so as to allow movement of the intermediate part 60 relative to the tool guide 11 according to the at least one additional degree of freedom in the second guiding configuration. Alternatively, when a slot is formed in the tool guide 11 and the pin or rib 65 is mounted so that it exits the tool guide channel 11 when the guiding system is in the second guiding configuration, the depth of the slot may correspond substantially to the dimension of the pin or rib 65 along the main direction. Indeed, as the pin or rib 65 has exited the tool guide 11 in the second guiding configuration, the slot does not risk preventing a movement of the intermediate part 60 according to the at least one additional degree of freedom.

FIGS. 12*a*, 12*b* and 12*c* illustrate non-limiting examples of blocking means 65, in the case when the tool 30 and the intermediate part 60 are adapted to be at least partially inserted inside the tool guide 11. The pin or rib 65 of FIGS. 12*a* and 12*b* is mounted on the intermediate part 60, between the first and second coupling links 21, 22. The pin or rib 65 of FIG. 12*c* is mounted on the first coupling link 21.

The tool 30 may be a drill adapted to drill a hole for example into a bone 310 of a patient 300. The drill can be moved in rotation around the tool axis T whatever the guiding configuration. The drill can also be moved according to the first degree of freedom in the first guiding configuration, or according to the first degree of freedom and/or the additional degree of freedom in the second guiding configuration.

The tool 30 may be a screwdriver having a handle 31 and a shaft 32 extending from the handle 31. The handle 31 of the screwdriver is adapted to be grasped by the user so as to move the screwdriver in rotation around the tool axis T whatever the guiding configuration, and also according to the first degree of freedom in the first guiding configuration, or according to the first degree of freedom and/or the additional degree of freedom in the second guiding configuration. The shaft 32 of the screwdriver extends substantially along the tool axis T. The intermediate part 60 may be mounted around the tool shaft 32 between the tool handle 31, which forms a proximal end of the tool 30, and a distal end of the tool 30 corresponding to a tip of the shaft 32 of the screwdriver, and may extend over at least part of the tool shaft 32.

The guiding system may further comprise a screw 33 adapted to be removably mounted on the tip of the shaft 32 of the screwdriver. Thus, the surgeon does not need to hold the screwdriver in one hand and the screw 33 in the other hand when performing the surgical operation. When the screw 33 is mounted on the tip of the shaft 32 of the screwdriver, the screw 33 extends substantially coaxially with the shaft 32 along the tool axis T, the screw 33 prolonging the screwdriver, and the screw 33 is considered to be part of the tool 30.

The screw 33 may be a pedicle screw, a one-piece screw, or a polyaxial screw. A dimension of the screw 33 may correspond substantially to a dimension of the surgical target channel 51 so that the screw 33 may be inserted, partially or substantially fully, inside the surgical target channel 51, as illustrated by way of a non-limiting example in FIG. 3 and in FIG. 6.

The tool guide 11 may comprise a tracker, also called tool guide tracker, adapted to be detected by a tracking system in order to determine a position and orientation of the tool guide 11 relative to a surgical target 50. The tool guide tracker is positioned and oriented in a fixed relation relative to the tool guide 11. Thus, a position and/or an orientation of the tool guide tracker relative to the tool guide 11 is fixed. The tool guide tracker may be mounted on the tool guide 11 or on any element of the surgical robotic system, such as a robotic arm 100, more specifically an end effector 10 of the robotic arm 100.

The tool guide tracker may be an optical, electromagnetic, ultrasonic, or inertial tracker.

The tracking system may be an optical-based tracking system, for example a camera such as an infrared camera, adapted to detect and localize, in terms of position and/or orientation, the tool guide tracker.

Thus, the relative position and orientation of the tool guide 11 and the surgical target 50 is known. The relative position and orientation of the tool 30 relative to the surgical target 50 may be deduced from parameters such as a position and/or orientation of the tool 30 relative to the tool guide 11, a dimension of the tool 30 along the tool guide axis X, a dimension of the connecting section 23, etc.

The tool guide tracker may be an optical tracker comprising several reflective markers, such as reflective disks or reflective spheres, arranged in at least one tracking pattern. The optical tool guide tracker is adapted to be localized, in terms of position and orientation, by the tracking system when the tracking system is within a range of visibility of at least one tracking pattern of the tool guide tracker.

The camera is adequately positioned before surgery, so that the whole area in which the surgical robotic system is likely to move during the surgical intervention is encompassed in the field of view of the camera. The camera detects and localizes the tool guide tracker, by detecting and localizing the reflective markers of the tracking pattern located in the field of view of the camera.

The tool 30 may comprise a tracker, also called tool tracker, adapted to be detected by a tracking system in order to determine a position and orientation of the tool 30 relative to the tool guide 11 and/or relative to the surgical target 50.

The tool tracker is mounted in a fixed relationship relative to the tool 30, for example mounted to the tool 30. Thus, a position and/or an orientation of the tool tracker relative to the tool 30 is known.

The tool tracker may be of a same or different nature to that of the tool guide tracker which is mounted on the tool guide 11, that is to say may be an optical, electromagnetic, ultrasonic, or inertial tracker. When the tool tracker and the tool guide tracker are optical trackers, a tracking pattern of the tool tracker is different from the tracking pattern of the tool guide tracker, so that the optical tracking system may differentiate the tool tracker from the tool guide tracker. The tracking system is thus adapted to detect, in terms of position and/or orientation, the tool guide tracker and the tool tracker.

For example, when the tool 30 is a screwdriver, the tool tracker may be mounted on the screwdriver, for example on the screwdriver shaft 32, in addition to the tool guide tracker which is mounted on the tool guide 11. The position and orientation of the tool tracker mounted on the screwdriver, for example the position and orientation of the tool tracker relative to the tip of the screwdriver shaft 32, is known. Thus, the position and/or orientation of the screwdriver relative to the surgical target 50 may be known when the tracking system acquires the tool tracker position.

The tool tracker mounted on the tool 30 may also serve to detect a misalignment between the tool 30 and the tool guide 11 before transitioning the guiding system from the second guiding configuration to the first guiding configuration. Thus, if such a misalignment is detected, it may be corrected, either manually by the user of the guiding system or automatically by the guiding system, so that the transition of the guiding system from the second guiding configuration to the first guiding configuration is not hindered or prevented by such a misalignment.

The guiding system may further comprise a patient tracker adapted to be positioned and/or oriented in a fixed relationship relative to a surgical target 50. The patient tracker is mounted in a fixed relationship relative to the surgical target 50. Thus, a position and/or an orientation of the patient tracker relative to the surgical target 50 is known.

The patient tracker may be of a same or different nature to that of the tool guide tracker which is mounted on the tool guide 11, that is to say may be an optical, electromagnetic, ultrasonic, or inertial tracker. When the patient tracker, the tool tracker if present, and the tool guide tracker are optical trackers, a tracking pattern of the patient tracker is different from the tracking patterns of the tool tracker and of the tool guide tracker, so that the optical tracking system may differentiate the patient tracker from the tool tracker and the tool guide tracker. The tracking system is thus adapted to detect, in terms of position and/or orientation, the patient tracker, the tool tracker if present, and the tool guide tracker.

Localizing the tool guide tracker and/or the tool tracker relative to the patient tracker allows the localization of the tool guide 11 and/or the tool 30 relative to the surgical target 50.

The patient tracker may be attached to an anatomical structure, for example to the skin or to a bone of the patient 300, and may be placed next to the surgical target 50.

When the patient tracker comprises one or more tracking patterns, each tracking pattern comprising at least one reflective marker, preferably at least four reflective markers, the patient tracker is positioned so that the localization system is within a range of visibility of at least one tracking pattern of the patient tracker. For example, the patient tracker may be positioned on the patient 300 before the surgical act. Thus, the patient tracker may be detected and localized at all times during surgery by the localization system.

A surgical robotic system, as illustrated by way of a non-limiting example in FIG. 1, may comprise a robotic arm 100 comprising the guiding system as disclosed above, a tracking system configured to determine a position and/or orientation of the tool guide 11 and/or the tool 30 relative to a surgical target 50, a control unit coupled to the tracking system and configured to control the robotic arm 100 to align the tool 30 with the surgical target 50, and a display unit 40 adapted to configure a guiding of the tool guide 11 and/or the tool 30.

The robotic arm 100 may comprise an end effector 10. The tool guide 11 is adapted to be mounted on the end effector 10. The robotic arm 100 may further comprise an end grip allowing manipulation of the robotic arm 100 by a user.

The display unit 40 may be configured so as to allow the user to plan the surgical intervention and/or to select a guiding configuration of the guiding system. The guiding system may be configured to automatically move the tool guide 11 and/or the tool 30 in order to achieve the desired configuration selected by the user. The display unit 40 may further be adapted to display information relative to the guiding of the tool 30 by the guiding system during the surgical intervention.

The surgical robotic system may comprise a base 400. The robotic arm 100 of the surgical robotic system is fixed to the base 400. The base 400 may be mobile on the ground, so that the user can move the base 400 in the operation room.

The surgical robotic system may comprise an imaging system 500, such as an X-ray imaging system comprising a C-arm. The imaging system 500 acquires 2D or 3D images of the patient 300 during the surgical procedure, so as to provide the surgeon with information about the anatomical situation of the patient 300 and/or the position and orientation of the tool 30 during surgery. The surgical robotic system comprising the imaging system 500 also comprises the tracking system configured to determine the position and orientation of the tool guide 11 and/or the tool 30 relative to a surgical target.

A method for guiding a tool 30 with a surgical robotic system as disclosed above relative to a surgical target 50, wherein the surgical target 50 comprises a surgical target channel 51 directed along a surgical target axis S, comprises the following steps:

S1: estimating a position of the tool 30 relative to the surgical target 50, comprising a step S11 of detecting, by a tracking system, at least one tool guide tracker mounted in a fixed relationship relative to the tool guide 11 and at least one patient tracker mounted in a fixed relationship relative to the surgical target 50;

S2: positioning the tool guide 11 so that the tool 30 is positioned at a predetermined distance from the surgical target channel 51;

S22: orienting the tool guide 11 so that the tool axis T is substantially aligned with the surgical target axis S;

S3: guiding the tool 30 in the first guiding configuration so as to partially insert said tool 30 inside the surgical target channel 51;

S4: guiding the tool 30 in the second guiding configuration so as to insert said tool 30 deeper inside the surgical target channel 51.

This method offers both a rigid guiding and a more flexible guiding of the surgical robotic system by the guiding system, thus presents substantially similar advantages to those described above concerning the guiding system. In particular, the method allows to minimize the workload of the surgeon while efficiently assisting the surgeon, in order to optimize the guiding and the final result of the surgical procedure.

Transitioning the surgical robotic system from the first guiding configuration to the second guiding configuration may be performed by translating along the tool guide axis X the first and second coupling links 21, 22 relative to the tool guide 11 along a predetermined transition length L4. In other words, the predetermined transition length L4 corresponds to the distance along the tool guide axis X that the first and second coupling links 21, 22 have to be moved so as to transition the guiding system from the first guiding configuration to the second guiding configuration. The predetermined transition length L4 may correspond to a few millimeters, or to a few centimeters.

The step S1 may comprise a step of detecting and localizing the tool guide tracker relative to the patient tracker. As the position and/or orientation of the tool guide 11 relative to the tool guide tracker is known and the position and/or orientation of the surgical target 50 relative to the patient tracker is known, the position and/or orientation of the tool 30 relative to the surgical target 50 can correspondingly be deduced.

The step S2 may be performed manually by a user of the surgical robotic system, or automatically by the surgical robotic system. During the positioning, the guiding system may be in the first guiding configuration. The tool 30 may be positioned so as to face the surgical target channel 51, a tip of the tool 30 being located on the surgical target axis S, the tool 30 being separated from the surgical target channel 51 by the predetermined distance. More specifically, the predetermined distance may be a distance in a direction of the surgical target axis S between the surgical target channel 51 and the tip of the tool 30.

Figure 9:
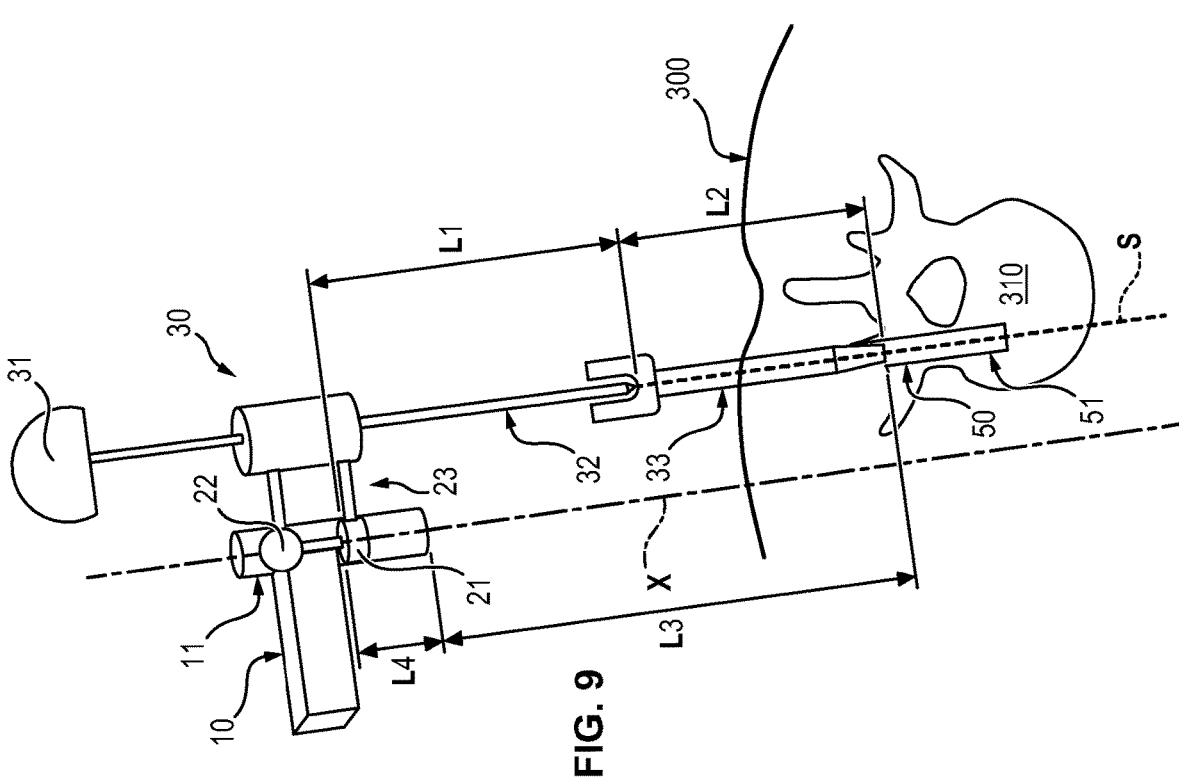

The predetermined distance is such that a position of a tip of the tool 30, for example a tip of the drill or a tip of the screw 33 mounted on the screwdriver, corresponds substantially to a position of the first end of the surgical target channel 51. For example, the tip of the screw 33 may be positioned substantially at the entry point into the bone 310 when the tool 30 is positioned at the predetermined distance from the surgical target channel 51. FIG. 9 illustrates a non-limiting example of a guiding system wherein the tool 30 is positioned at the predetermined distance from the surgical target channel 51, the tip of the screw 33 being positioned substantially at the entry point into the bone 310.

The step S22 may be performed manually by a user of the surgical robotic system, or automatically by the surgical robotic system. In the non-limiting example of FIG. 9, the tool 30, the intermediate part 60 and the tool guide 11 are substantially parallel to each other, the tool guide axis X and the tool axis T being parallel, and the tool axis T is aligned with, that is to say substantially coincides with, the surgical target axis S.

The step S3 of guiding the surgical robotic system in the first guiding configuration allows a rigid guiding of the tool 30 relative to the surgical target 50, the guiding system being in the first guiding configuration. The guiding may be performed in step S3 so as to reduce a distance between the tool 30 and the surgical target channel 51 and/or so as to partially insert the tool 30 inside the surgical target channel 51.

More specifically, the step S3 may correspond to a translation of the tool 30 along the tool guide axis X of a distance corresponding substantially to the predetermined transition length L4 and may further include a rotation of the tool 30 around the tool axis T. Thus, if the tip of the tool 30 is positioned substantially at the first end of the surgical target channel 51 in step S2, then during step S3, the tool 30 is inserted inside the surgical target channel 51 along a distance which corresponds to the predetermined transition length L4. For example, the drill is inserted inside the bone 310, or the screw 33 is inserted inside the drilled hole, along a distance which corresponds to the predetermined transition length L4. At the end of step S3, the tool 30 is partially inserted in the surgical target channel 51, and the guiding system transitions from the first guiding configuration to the second guiding configuration.

The surgical target channel 51 may present a length along the surgical target axis S which is greater than the predetermined transition length L4. Thus, a transition between the first guiding configuration and the second guiding configuration of the guiding system occurs when the tool 30, such as the screw 33 mounted on the screwdriver, or the drill, is inserted inside the surgical target channel 51 along the predetermined transition length L4, the screw 33 or drill being partially inserted inside the surgical target channel 51.

Figure 10:
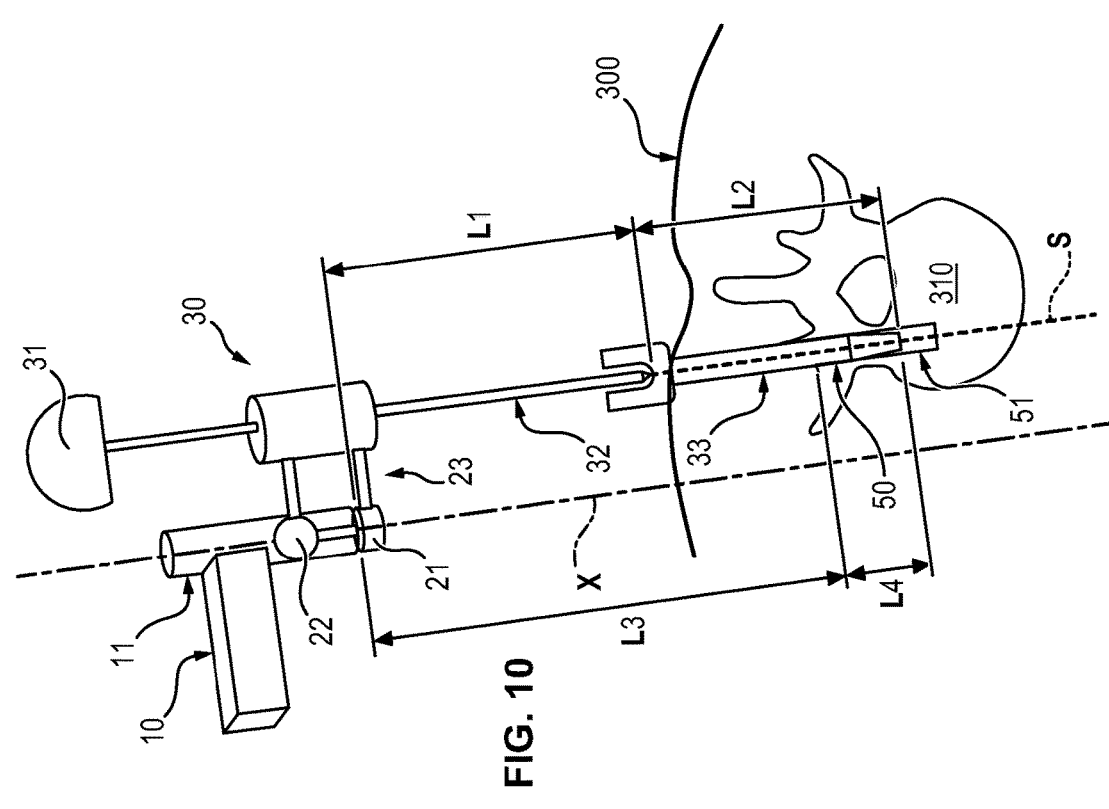
FIGS. 9 and 10 are perspective views of guiding systems for a surgical robotic system according to an embodiment of the invention, the guiding system being respectively in the first guiding configuration and in the second guiding configuration.

FIG. 10 illustrates a non-limiting example of a guiding system having just transitioned to the second guiding configuration, the guiding system comprising a screw 33 which is partially inserted in the surgical target channel 51.

Figure 3:
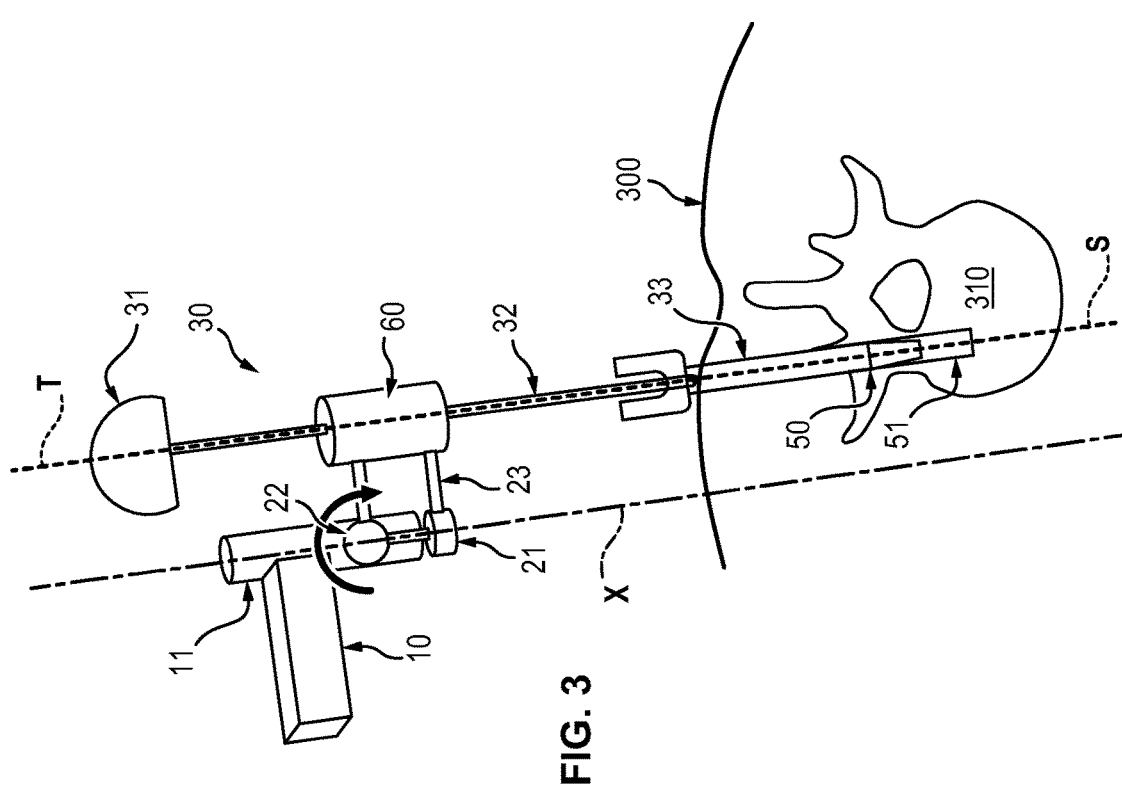
FIG. 3 is a perspective view of a guiding system for a surgical robotic system according to an embodiment of the invention, the guiding system being in the second guiding configuration.
Figure 2:
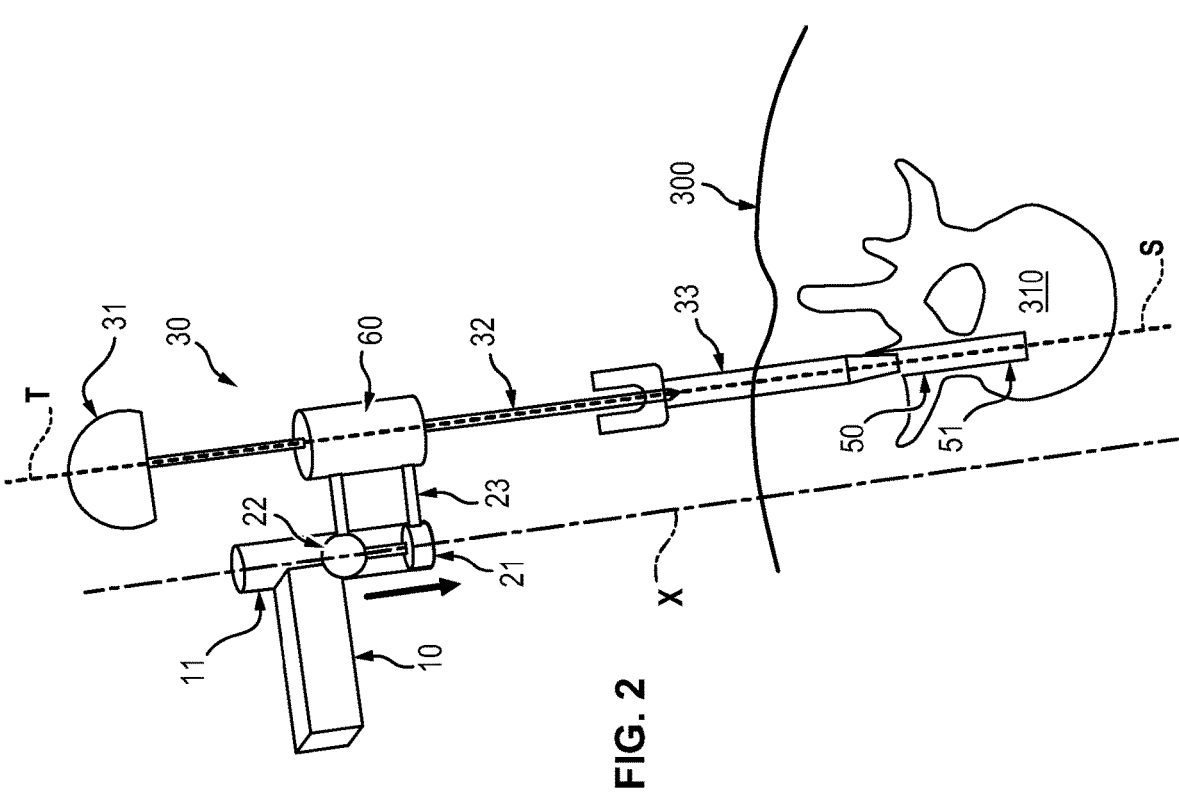
FIG. 2 is a perspective view of a guiding system for a surgical robotic system according to an embodiment of the invention, the guiding system being in the first guiding configuration.
Figure 6:
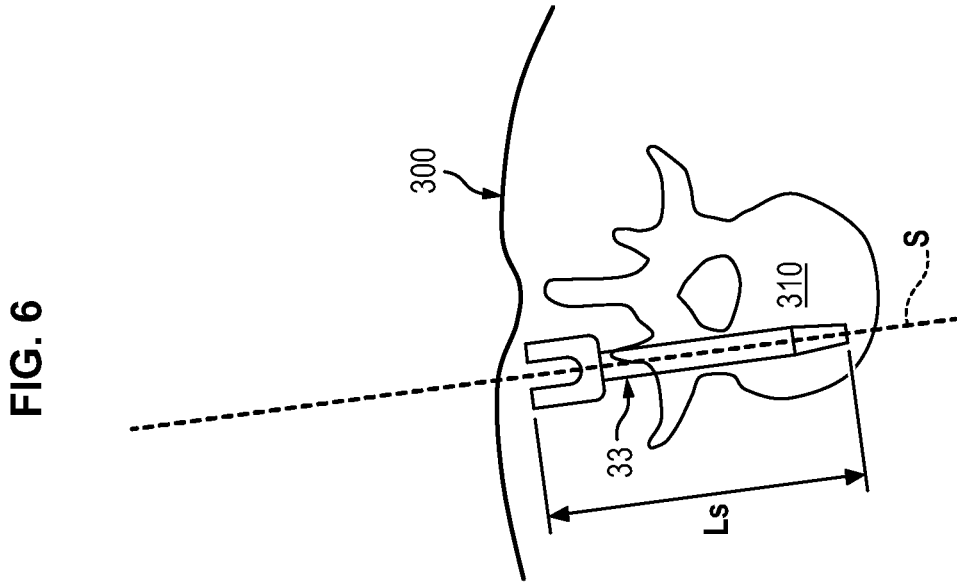

The step S4 of guiding the surgical robotic system in the second guiding configuration allows a more flexible guiding of the tool 30 relative to the surgical target 50, in order to insert the tool 30 deeper inside the surgical target channel 51. FIG. 3 illustrates a non-limiting example of a surgical robotic system in a configuration where the screw 33 is partially inserted in the surgical target channel 51 and the guiding system is in the second guiding configuration, the second guiding configuration allowing a translation of the tool 30 relative the tool guide 11 along the tool guide axis X and an inclination of the tool 30 relative the tool guide axis X, as well as the rotation of the tool 30 around the tool axis T. FIG. 6 illustrates a surgical target channel 51 into which a screw 33 is fully inserted.

The step S4 of guiding the surgical robotic system in the second guiding configuration may comprise a step S41 of adjusting a relative position and/or orientation of the tool 30 with respect to the surgical target 50 in the at least one additional degree of freedom, wherein said step S41 is performed manually by a user of the surgical robotic system.

The predetermined distance from the surgical target channel 51 at which the tool 30 is positioned in step S2 may correspond to a distance L3 between the tool guide 11 and the surgical target channel 51, more specifically to a distance L3 between the distal end of the tool guide 11 and the first end of the surgical target channel 51 during said step S2.

The predetermined distance at which the tool 30 is positioned in step S2 may be determined depending at least on a length of the tool L1+L2. The length of the tool L1+L2 corresponds to a distance between a tip of the tool 30 and a proximal end of the first coupling link 21, 22, more specifically to a distance between the tip of the tool 30 and the additional coupling link of the first coupling link 21, 22. A position of the proximal end of the first coupling link 21, 22 may substantially correspond to a proximal position of the connecting section 23, the connecting section 23 extending radially outwardly from the shaft 32 to mechanically connect the first and second coupling links 21, 22 to the tool 30.

The length of the tool L1+L2 may be known, or may be determined based on the acquisition of the tool guide tracker and/or the tool tracker by the tracking system.

When the tool 30 is a drill, the length of the tool L1+L2 corresponds to a distance between a tip of the drill and a proximal end of the first coupling link 21, 22. When the tool 30 is a screwdriver having a handle 31 and a shaft 32 extending from the handle 31, the tool 30 is considered to include the screw 33 mounted to the tip of the shaft 32 of the screwdriver. The length of the tool L1+L2 corresponds to a distance between the tip of the screw 33 mounted on the screwdriver and the proximal end of the first coupling link 21, 22. The length of the tool L1+L2 thus corresponds to a sum of a distance between the proximal end of the first coupling link 21, 22 to the tip of the shaft 32 of the screwdriver L1, and a length of the screw L2.

The predetermined distance from the surgical target channel 51 at which the tool 30 is positioned in step S2 is thus further determined depending on the length of the screw L2. The length of the screw L2 may correspond to a distance between the tip of the screwdriver and a tip of the screw 33 when the screw 33 is mounted on the screwdriver. The length of the screw L2 may be known, for example may be retrieved from a planning of the surgical procedure. The length L1 of the screwdriver may be fixed.

The tool 30 may be positioned in step S2 so that a tip of the screw 33, or so that a tip of the drill, substantially coincides with the first end of the surgical target channel 51, as illustrated for example in FIG. 9. A position of the first end of the surgical target channel 51, which corresponds to the position of the surgical target channel 51, may be known, for example may be retrieved from the planning of the surgical procedure.

The tool 30 is thus moved towards the first end of the surgical target 50, so that the tip of the tool 30 coincides with the first end of the surgical target channel 51 at the end of step S2. The tool 30 can then be inserted in the surgical target channel 50 in steps S3 and S4, towards the second end of the surgical target channel 50.

The distance between the tool guide 11 and the surgical target channel 51 may be determined during the surgical procedure based on the acquisition of the tool guide tracker and/or the patient tracker by the tracking system, and may be controlled by the command of the surgical robotic system.

A length of guiding in first guiding configuration corresponds substantially to the predetermined transition length L4.

The predetermined transition length L4 corresponds to a distance between the distal end of the tool guide 11 and the first coupling link 21, 22, more specifically between the distal end of the tool guide 11 and the proximal end of the additional coupling link of the first coupling link 21, 22, when the tool 30 and tool guide 11 are positioned at the beginning of the surgical procedure.

The predetermined transition length L4 may be equal to 0, in order to begin the surgical procedure with a system in the second guiding configuration. During the surgical procedure, the system may punctually transition from the second guiding configuration to the first guiding configuration.

The predetermined transition length L4 may be inputted by the user of the surgical robotic system before the surgery. The input of the predetermined transition length L4 may be done through a main interface of the surgical robotic system, typically a touch screen interface that allows the surgeon to plan the surgical procedure, follow the navigation and set up other parameters of the surgical systems. In the case of the predetermined transition length L4, it may be inputted during the planning phase.

The predetermined distance at which the tool 30 is positioned in step S2 may also be inputted by the user of the surgical robotic system before the surgery, for example during the planning phase.

During step S2, the tool 30 may be positioned such that the length of the tool L1+L2 corresponds substantially to a sum of the predetermined distance at which the tool 30 is positioned in step S2, which corresponds during step S2 to the distance L3 between the tool guide 11 and the surgical target channel 51, and the predetermined transition length L4: L1+L2=L3+L4.

The invention claimed is:

1. A guiding system for a surgical robotic system, comprising a tool guide extending substantially around a tool guide axis, a tool extending substantially around a tool axis, an intermediate part mounted on the tool so that the tool and the intermediate part are integral in translation and so that the tool is mobile relative to the intermediate part in rotation around the tool axis, and first and second coupling links adapted to couple the intermediate part and the tool guide, wherein the guiding system presents:

a first guiding configuration in which the first coupling link couples the intermediate part and the tool guide so that the intermediate part and the tool guide are mobile relative to each other according to a unique first degree of freedom, the first degree of freedom corresponding to a translation along the tool guide axis; and a second guiding configuration in which the second coupling link couples the intermediate part and the tool guide so that the intermediate part and the tool guide are mobile relative to each other according to the first degree of freedom and according to at least one additional degree of freedom.

2. The guiding system of claim 1, wherein the at least one additional degree of freedom comprises an inclination of the tool relative to the tool guide axis.

3. The guiding system of claim 1, wherein the at least one additional degree of freedom comprises a translation of the tool in a plane perpendicular to the tool guide axis.

4. The guiding system of claim 3, wherein the second coupling link is at least partially made of an elastic material, such that a deformation of said elastic material of the second coupling link allows said translation of the tool in the plane perpendicular to the tool guide axis.

5. The guiding system of claim 1, wherein at least one of the first coupling link and the second coupling link includes a slide link, wherein the slide link is directed along the tool guide axis.

6. The guiding system of claim 1, wherein at least one of the first coupling link and the second coupling link includes a ball joint.

7. The guiding system of claim 1, wherein the first coupling link includes the second coupling link and an additional coupling link.

8. The guiding system of claim 1, wherein the tool is a screwdriver having a handle and a shaft extending from the handle.

9. The guiding system of claim 1, wherein at least one of the first and second coupling links and the intermediate part are rigidly secured to each other so as to be moved together.

10. The guiding system of claim 1, wherein the first and second coupling links are configured so that a transition between the first guiding configuration and the second guiding configuration is achieved by translating the first and second coupling links relative to the tool guide along the tool guide axis.

11. The guiding system of claim 1, wherein the first coupling link is adapted to be located inside the tool guide in the first guiding configuration and at least partially outside the tool guide in the second guiding configuration.

12. The guiding system of claim 1, wherein the tool and the intermediate part are adapted to be at least partially inserted substantially radially inside the tool guide, the first and second coupling links being arranged on the intermediate part.

13. The guiding system of claim 1, wherein the tool is adapted to be mounted radially outside the tool guide, the first and second coupling links being at least partially inserted in sliding engagement within the tool guide and comprising a connecting section extending radially outwardly to mechanically connect the first and second coupling links to the intermediate part.

14. The guiding system of claim 1, further comprising a blocking mechanism adapted to prevent a rotation of the intermediate part relative to the tool guide around the tool axis.

15. The guiding system of claim 1, wherein the tool guide comprises a tracker adapted to be detected by a tracking system in order to determine a position and orientation of the tool guide relative to a surgical target.

16. The guiding system of claim 15, wherein the tool comprises a tracker adapted to be detected by the tracking system in order to determine a position and orientation of the tool relative to at least one of the tool guide and the surgical target.

17. A surgical robotic system, comprising:

a robotic arm comprising the guiding system of claim 15, a tracking system configured to determine a position and orientation of at least one of the tool guide and the tool relative to a surgical target, a control unit coupled to the tracking system and configured to control the robotic arm to align the tool with the surgical target, and a display unit adapted to configure a guiding of at least one of the tool guide and the tool.

18. A method for guiding a tool with the surgical robotic system of claim 17 relative to a surgical target, wherein the surgical target comprises a surgical target channel directed along a surgical target axis, the method comprising:

S1: estimating a position of the tool relative to the surgical target, comprising a step S11 of detecting, by a tracking system, at least one tool guide tracker mounted in a fixed relationship relative to the tool guide and at least one patient tracker mounted in a fixed relationship relative to the surgical target;

S2: positioning the tool guide so that the tool is positioned at a predetermined distance from the surgical target channel;

S22: orienting the tool guide so that the tool axis is substantially aligned with the surgical target axis;

S3: guiding the tool in the first guiding configuration so as to partially insert said tool inside the surgical target channel;

S4: guiding the tool in the second guiding configuration so as to insert said tool deeper inside the surgical target channel.

19. The method of claim 18, wherein guiding the surgical robotic system in the second guiding configuration comprises:

S41: manually adjusting, by a user of the surgical robotic system, at least one of a relative position and orientation of the tool with respect to the surgical target in the at least one additional degree of freedom.

20. The method of claim 18, comprising transitioning the surgical robotic system from the first guiding configuration to the second guiding configuration by translating the first and second coupling links along the tool guide axis relative to the tool guide according to a predetermined transition length.

21. The method of claim 20, further comprising determining the predetermined distance from the surgical target channel at which the tool is positioned depending at least on a length of the tool and a length of guiding in first guiding configuration, wherein the length of guiding in first guiding configuration corresponds substantially to the predetermined transition length.

22. The method of claim 18, wherein the tool is a screwdriver having a handle and a shaft extending from the handle, the guiding system further comprising a screw adapted to be removably attached to a tip of the shaft, wherein the predetermined distance from the surgical target channel at which the tool is positioned is further determined depending on a length of the screw.

* * * * *